United States Patent
Watanabe (10) Patent No.: US 9,745,386 B2
(45) Date of Patent: Aug. 29, 2017

(54) ANTI-CHONDROITIN-SULFATE-E ANTIBODY

(71) Applicant: SEIKAGAKU CORPORATION, Chiyoda-ku, Tokyo (JP)

(72) Inventor: Ippei Watanabe, Tokyo (JP)

(73) Assignee: SEIKAGAKU CORPORATION, Tokyo (JP)

(*) Notice: Subject to any disclaimer, the term of this patent is extended or adjusted under 35 U.S.C. 154(b) by 0 days.

(21) Appl. No.: 15/128,913

(22) PCT Filed: Mar. 31, 2015

(86) PCT No.: PCT/JP2015/060226
§ 371 (c)(1),
(2) Date: Sep. 23, 2016

(87) PCT Pub. No.: WO2015/152280
PCT Pub. Date: Oct. 8, 2015

(65) Prior Publication Data
US 2017/0107301 A1   Apr. 20, 2017

(30) Foreign Application Priority Data

Mar. 31, 2014 (JP) ................................. 2014-072431
Aug. 8, 2014 (JP) ................................. 2014-162968

(51) Int. Cl.
*G01N 33/53* (2006.01)
*C07K 16/44* (2006.01)

(52) U.S. Cl.
CPC .......... *C07K 16/44* (2013.01); *G01N 33/5308* (2013.01); *C07K 2317/14* (2013.01); *C07K 2317/92* (2013.01); *G01N 2400/40* (2013.01)

(58) Field of Classification Search
CPC ............ A61K 2039/505; A61K 31/737; A61K 39/39558; G01N 2400/40; G01N 33/5308; C07K 16/44; C07K 2317/14; C07K 2317/92
See application file for complete search history.

(56) References Cited

U.S. PATENT DOCUMENTS

2003/0153492 A1   8/2003   Danishefsky et al.
2008/0009607 A1   1/2008   Tully et al.
2010/0324271 A1   12/2010  Yamaguchi et al.

FOREIGN PATENT DOCUMENTS

JP   09-12600 A    1/1997
JP   2006-129701 A 5/2006
WO   WO 90/06954 A1 6/1990

OTHER PUBLICATIONS

Fukui et al., "Oligosaccharide microarrays for high-throughput detection and specificity assignments of carbohydrate-protein interactions," *Nature Biotechnology*, vol. 20, pp. 1011-1017 (Oct. 2002).
International Search Report for International Application No. PCT/JP2015/060226, mailed on Jun. 30, 2015.
Ito et al., "Structural characterization of the epitopes of the monoclonal antibodies 473HD, CS-56, and MO-225 specific for chondroitin sulfate D-type using the oligosaccharide library," *Glycobiology*, vol. 15(6), pp. 593-603 (2005).
Smetsers et al., "Human Single-Chain Antibodies Reactive with Native Chondroitin Sulfate Detect Chondroitin Sulfate Alterations in Melanoma and Psoriasis," *Journal of Investigative Dermatology*, vol. 122, pp. 707-716 (2004).
Sugahara et al., "Chapter 3, ISCSM2011 Chondroitin Sulfate E-type Structure at Tumor Cell Surface Is Involved in Experimental Metastasis," *Advances in Experimental Medicine and Biology*, vol. 749, pp. 33-45 (2012).
Ten Dam et al., "Antibody GD3G7 Selected against Embryonic Glycosaminoglycans Defines Chondroitin Sulfate-E Domains Highly Up-Regulated in Ovarian Cancer and Involved in Vascular Endothelial Growth Factor Binding," *The American Journal of Pathology*, vol. 171(4), pp. 1324-1333 (Oct. 2007).
Yamagata et al., "A Monoclonal Antibody That Specifically Recognizes a Glucuronic Acid 2-Sulfate-containing Determinant in Intact Chondroitin Sulfate Chain," *The Journal of Biological Chemistry*, vol. 262(9), pp. 4146-4152 (Mar. 25, 1987).

*Primary Examiner* — Shafiqul Haq
*Assistant Examiner* — Carmencita M Belei
(74) *Attorney, Agent, or Firm* — Knobbe, Martens, Olson & Bear LLP (57) ABSTRACT

The present invention provides an antibody that can react with chondroitin sulfate E at a high specificity and that can be used for, for example, the detection, isolation, and so forth, of specific sulfated polysaccharides. The present invention relates to a novel anti-chondroitin sulfate E antibody that reacts with chondroitin sulfate E and does not react with chondroitin sulfate A, does not react with chondroitin sulfate B, and does not react with chondroitin sulfate D.

8 Claims, 2 Drawing Sheets

E-12C Antibody     E-18H Antibody

[Fig. 4]

E-12C Antibody     E-18H Antibody

[Fig. 5]

Without C-ABC treatment   With C-ABC treatment   Negative control (mouse IgM)

ANTI-CHONDROITIN-SULFATE-E ANTIBODY

CROSS-REFERENCE TO RELATED APPLICATIONS

This application is the U.S. National Phase under 35 U.S.C. §371 of International Application PCT/JP2015/060226, filed Mar. 31, 2015, which claims priority to JP Application No. 2014-072431, filed Mar. 31, 2014 and JP Application No. 2014-162968, filed Aug. 8, 2014.

TECHNICAL FIELD

The present invention relates to a novel anti-chondroitin sulfate E antibody that reacts with chondroitin sulfate E but does not react with chondroitin sulfate A, does not react with chondroitin sulfate B, and does not react with chondroitin sulfate D.

BACKGROUND ART

The following abbreviations are used in the text of this application.
CSA: chondroitin sulfate A
CSB: chondroitin sulfate B
CSC: chondroitin sulfate C
CSD: chondroitin sulfate D
CSE: chondroitin sulfate E
DS: dermatan sulfate
Hep: heparin
HS: heparan sulfate
HPN: heparosan
KS: keratan sulfate
HA: hyaluronic acid
deS-CSC: fully desulfated chondroitin sulfate C
de6S-CSE: 6-O-desulfated chondroitin sulfate E
CS: chondroitin sulfate
GAG: glycosaminoglycan
GlcA: glucuronic acid
IdoA: iduronic acid
GalNAc: N-acetylgalactosamine
PE: dipalmitoyl-L-(α-phosphatidyl)ethanolamine
C-ABC: chondroitinase ABC
PBS: phosphate-buffered saline
CSE-PE: dipalmitoyl-L-(α-phosphatidyl)ethanolamine-linked chondroitin sulfate E CS is a type of GAG and is a linear polymeric polysaccharide composed of a repeating disaccharide structure of GlcA and GalNAc. Differences in the number of sulfate groups bonded to the disaccharide unit and in their bonding positions and the existence of uronic acid isomers cause a variety of CS structures to exist. The isomers of CS include CSA, CSB (also known as DS), CSC, CSD, CSE, etc.

CSE is a sulfated polysaccharide that has a repeat structure of the basic disaccharide unit [GlcAβ1-3GalNAc(4S,6S)] of GlcA and GalNAc that has undergone modification by sulfation at its 4 position and 6 position.

The following, for example, are known as antibodies which react with CSE: the Ch-1 antibody and Ch-3 antibody, which are reported to react with CSE and CSB which has a repeat structure of the basic disaccharide unit [IdoAβ1-3GalNAc(4S)] (Patent Literature 1); the MO-225 antibody, which is reported to mainly recognize the D type structure [GlcA(2S)β1-3GalNAc(6S)] that is the basic disaccharide unit of CSD, but also to react with CSE (Non Patent Literature 1, 2, and 3); and the GD3G7 antibody, which is reported to react with CSE, shark skin-derived DS, and CSA (Non Patent Literature 4).

CITATION LIST

Patent Literature

[PTL 1] Japanese Patent Application Publication No. 2006-129701

Non Patent Literature

[Non Patent Literature 1] Masahito Yamagata et al., "Journal of Biological Chemistry", Volume 262, Number 9, Mar. 25, 1987, pp. 4146-4152
[Non Patent Literature 2] Yumi Ito et al., "Glycobiology", Volume 15, Number 6, 2005, pp. 593-603
[Non Patent Literature 3] Shigeyuki Fukui et al., "Nature Biotechnology", Number 20, 2002, pp. 1011-1017
[Non Patent Literature 4] Gerdy B. ten Dam et al., "The American Journal of Pathology", Volume 171, Number 4, October, 2007, pp. 1324-1333

SUMMARY OF INVENTION

Technical Problem

The problem for the present invention is to provide an antibody that can react with CSE at a high specificity and that can be used for, for example, the detection, isolation, and so forth, of specific sulfated polysaccharides.

Solution to Problem

In pursuit of a solution to this problem, the present inventor sought to produce a novel anti-CSE antibody using as antigen a substance in which a lipid is linked to CSE.

As a result of focused investigations, the present inventor discovered that the antibody that was obtained reacts with CSE but does not react with CSA, does not react with CSB, and does not react with CSD and thus achieved the invention of an anti-CSE antibody that specifically reacts with CSE.

Thus, the present invention is as follows.

(1) An antibody that reacts with chondroitin sulfate E and does not react with chondroitin sulfate A, does not react with chondroitin sulfate B, and does not react with chondroitin sulfate D.

(2) The antibody according to (1), which also does not react with any of chondroitin sulfate C, fully desulfated chondroitin sulfate C, heparin, heparan sulfate, heparosan, keratan sulfate, hyaluronic acid, and 6-O-desulfated chondroitin sulfate E.

(3) The antibody according to (1) or (2), which does not react with sulfated chondroitin sulfate B.

(4) The antibody according to any of (1) to (3), which is obtained by carrying out an immunization using as antigen a substance in which a lipid is linked to chondroitin sulfate E.

(5) The antibody according to (4), wherein the lipid is dipalmitoyl-L-(α-phosphatidyl)ethanolamine.

(6) The antibody according to any of (1) to (5), which is a monoclonal antibody.

(7) A monoclonal antibody produced by a hybridoma having receipt number NITE ABP-01808 or NITE ABP-01809.

(8) A hybridoma that produces the monoclonal antibody according to (6).

(9) The hybridoma according to (8), which is formed by cell fusion between a tumor cell and an antibody-producing cell originating from an animal that has been immunized using as antigen a substance in which a lipid is linked with chondroitin sulfate E.

(10) The hybridoma according to (9), wherein the lipid is dipalmitoyl-L-(α-phosphatidyl)ethanolamine.

(11) A hybridoma having receipt number NITE ABP-01808 or NITE ABP-01809.

(12) A method of detecting chondroitin sulfate E present in a sample, containing at least a step of bringing the antibody according to any of (1) to (7) into contact with the sample.

(13) A detection kit for chondroitin sulfate E, containing at least the antibody according to any of (1) to (7).

(14) A method of producing an antibody that reacts with chondroitin sulfate E and does not react with chondroitin sulfate A, does not react with chondroitin sulfate B, and does not react with chondroitin sulfate D, containing at least a step of carrying out an immunization using as antigen a substance in which a lipid is linked with chondroitin sulfate E.

(15) The method according to (14), wherein the lipid is dipalmitoyl-L-(α-phosphatidyl)ethanolamine.

Advantageous Effects of Invention

Because of specifically reacting with CSE, the antibody of the present invention can be favorably used for the detection of CSE. In addition, the antibody of the present invention can be efficiently produced using the hybridoma of the present invention. CSE can be very accurately detected by using the CSE detection method of the present invention. Moreover, the detection of CSE using the CSE detection method of the present invention can be carried out more efficiently, simply, and conveniently by using the CSE detection kit of the present invention.

DESCRIPTION OF EMBODIMENTS

The present invention is described in further detail in the following.

The present invention provides an antibody that reacts with CSE and does not react with CSA, does not react with CSB, and does not react with CSD.

CSE is a sulfated polysaccharide that has a repeat structure of the basic disaccharide unit [GlcAβ1-3GalNAc(4S, 6S)] of GlcA and GalNAc that has undergone modification by sulfation at its 4 position and 6 position. The CSE with which the antibody of the present invention reacts may, as long as it is such a sulfated polysaccharide, be a natural CSE or a chemically synthesized CSE. Natural CSE can be exemplified by CSE from squid. Chemically synthesized CSE can be exemplified by CSE chemically synthesized from CSA by the method described in Example 6(1) below (also referred to in the following as sulfated CSA). The occurrence ratio of the aforementioned basic disaccharide unit in such a CSE is preferably at least 15%, more preferably at least 30%, still more preferably at least 40%, very preferably at least 50%, particularly preferably at least 60%, and most preferably at least 70%. The occurrence ratio for the basic disaccharide unit can be determined by the method described in the examples below.

Unless specifically indicated otherwise, "reaction" of an antibody in the present invention refers to an immunological reaction or an antigen-antibody reaction and can be evaluated through binding with an antigen. The binding between the antibody and antigen can be examined by common methods, e.g., the ELISA method, RIA method, plaque method, agglutination reaction method, flow cytometry method, tissue staining method, western blot method, and surface plasmon resonance method. The ELISA method can be exemplified by the method described in Example 3(2) below. For example, when the ELISA method is run using an antibody, a reaction by the antibody with the antigen can be concluded to occur when the reaction signal increases in proportion to an increase in the antigen concentration.

In addition, the reactivity of the antibody of the present invention for an antigen can be considered, for example, in terms of the relative reactivity based on the reactivity of the antibody of the present invention for CSE as measured by the method described in Example 3(2) below.

In the Description of the present application, "does not react" means that the reactivity between an antigen and an antibody is approximately the same as the negative control or blank. For example, in the aforementioned method for measuring the reactivity, and using 100% for the reactivity with CSE, an evaluation of "does not react" can be made when the difference between the antigen-antibody reactivity and the negative control or blank is less than 10%, preferably less than 5%, more preferably less than 4%, even more preferably less than 3%, very preferably less than 2%, particularly preferably less than 1%, and most preferably less than 0.5%.

The antibody of the present invention is an antibody that reacts with CSE and does not react with CSA, does not react with CSB, and does not react with CSD, but is not otherwise particularly limited; however, it is preferably an antibody that also does not react with CSC, deS-CSC, Hep, HS, HPN, KS, HA and de6S-CSE and is more preferably an antibody that also does not react with sulfated CSB.

Here, sulfated CSB refers to the product obtained by the method described in Example 6(1) below.

The class of the antibody is not particularly limited, but it is preferably IgM and even more preferably is the IgM, κ chain.

The type of the antibody of the present invention is not particularly limited, and it may be a monoclonal antibody or a polyclonal antibody, but it is preferably monoclonal antibody. The monoclonal antibody may be a portion of an antibody, i.e., it may be an antibody fragment. This antibody fragment can be exemplified by Fab, F(ab')$_2$, Fab', Fv, and so forth. The antibody fragment can be obtained, for example, by digestion of the monoclonal antibody with, for example, a peptidase. For example, the Fab fragment can be obtained by treating the monoclonal antibody of the present invention with papain, while the F(ab')$_2$ fragment can be obtained by treating the monoclonal antibody of the present invention with pepsin.

Methods for obtaining the antibody of the present invention will be described using the divisions given below. However, the method of obtaining the antibody of the present invention is not limited to or by the following.

1. Preparation of the antigen
2. Immunization method
3. Acquisition of the polyclonal antibody
4. Acquisition of the monoclonal antibody
5. Preparation of Hybridomas
6. Hybridoma selection and cloning <1. Preparation of the Antigen>

In order to raise the antigenicity of the CSE, for example, the antibody of the present invention can be obtained by immunizing an animal capable of producing antibodies, using as antigen a substance provided by linking CSE to a lipid. The CSE is not particularly limited, but squid-derived CSE is preferred. The lipid is not particularly limited as long as it can link to CSE, but phospholipids are preferred and PE is more preferred. The linkage between the lipid and CSE is not particularly limited, but chemical bonding is preferred, covalent bonding is more preferred, and an aminoalkyl linkage is still more preferred. The PE/GAG-linking method that can be used to link PE to CSE can be exemplified by the method described in Japanese Patent Application Publication No. H4-80201, in which a reducing terminal is converted into a lactone; the method described in Japanese Patent Application Publication No. H4-80202, in which a reducing terminal is subjected to a limited oxidation; and the method described in Japanese Patent Application Publication No. 2003-335801, in which preparation proceeds via a GAG-tetrabutylammonium (GAG-But$_4$N$^+$) salt.

<2. Immunization Method>

The animal to be immunized should be an animal capable of producing antibody that reacts with CSE, but is not otherwise particularly limited; however, animals such as the pig, cow, rabbit, sheep, chicken, rat, and mouse are preferred and the mouse is preferred.

An immunological adjuvant may in particular not be used; however, when an adjuvant is used, an adjuvant for which an adjuvant effect can be expected is preferred, e.g., alum, Gram-positive bacteria, Gram-negative bacteria, and nucleic acids, with Salmonella cell membrane being more preferred.

The immunization can be carried out, for example, by intravenous injection of the antigen and adjuvant into the animal. The injection method is not limited to this, and may be subcutaneous injection or intraperitoneal injection. Immunization is ordinarily carried out divided into a plurality of times.

<3. Acquisition of the Polyclonal Antibody>

The polyclonal antibody can be acquired by collecting blood from an immunized animal. Whether the polyclonal antibody is present in the collected blood can be evaluated using an antibody reaction as the indicator. Methods for measuring the antibody reaction can be exemplified by the ELISA method, RIA method, plaque method, agglutination reaction method, flow cytometry method, tissue staining method, and western blot method. The polyclonal antibody may be the collected blood itself, or may be the serum obtained by centrifugal separation, or may be purified polyclonal antibody. Antibody purification can be achieved by a suitable combination of biochemical techniques such as, salting out, ion exchange, gel filtration, affinity chromatography, electrophoresis, and so forth.

<4. Acquisition of the Monoclonal Antibody>

The method for acquiring the monoclonal antibody can be exemplified by methods in which the obtained hybridoma is cultured in vitro or in vivo and can be selected in correspondence to the objective. In the in vitro case the monoclonal antibody can be obtained by recovering the cell culture liquid from the hybridoma culture; in the in vivo case it can be obtained from the ascites of the mouse into which the hybridoma was transplanted.

The cell culture liquid itself or ascites themselves may be used as the monoclonal antibody; or the product obtained by, for example, the centrifugal removal of the cells, may be used as the monoclonal antibody; or a purified product may be used as the monoclonal antibody.

Antibody purification can be achieved by a suitable combination of biochemical techniques such as, salting out, ion exchange, gel filtration, affinity chromatography, electrophoresis, and so forth.

CSE-reactive monoclonal antibody can be exemplified by the monoclonal antibodies produced from the hybridomas designated E-12C and E-18H (referred to hereafter as the E-12C antibody and the E-18H antibody).

A characteristic feature of the E-12C antibody and the E-18H antibody is that they react with CSE but do not react with various other GAGs (CSA, CSB, CSC, CSD, deS-CSC, Hep, HS, HPN, KS, HA, de6S-CSE, sulfated CSB).

<5. Preparation of Hybridomas>

The hybridoma is produced by cell fusion between tumor cells and antibody-producing cells obtained by the removal of lymph nodes or the spleen from the immunized animal. The antibody-producing cells are preferably lymphocytes. The tumor cells are preferably myeloma cells and, with regard to origin, are preferably of mammalian origin and are more preferably of murine origin.

<6. Hybridoma Selection and Cloning>

Hybridoma selection can be carried out using, for example, the hybridoma growth rate and the antibody reaction as indicators. The method for measuring the antibody reaction can be exemplified by the ELISA method, RIA method, plaque method, agglutination reaction method, flow cytometry method, tissue staining method, western blot method, surface plasmon resonance method, etc.

Hybridomas that produce CSE-reactive antibody are selected using the methods indicated above and cloning is carried out on the obtained hybridomas. The cloning method can be exemplified by the limiting dilution method and so forth. In the limiting dilution method, a 96-well plate is preferably seeded such that the number of cells per 1 well is 1/well (5.0 cells/mL) or 0.5/well (2.5 cells/mL). The cloning process is preferably repeated at least two times and a monoclone is preferably prepared.

Specific hybridomas can be exemplified by the hybridomas designated E-12C and E-18H.

These hybridomas were deposited on Feb. 26, 2014 (deposition date) with the NITE Patent Microorganisms Depositary (NPMD) (Room 122, 2-5-8 Kazusakamatari, Kisarazu-shi, Chiba 292-0818, Japan) and were given accession numbers NITE P-01809 and NITE P-01808, respectively. In addition, these were transferred to international depositions under the Budapest Treaty on Feb. 17, 2015 (Accession numbers NITE BP-01809 and NITE BP-01808).

The CSE detection method of the present invention contains a step of bringing a sample into contact with the antibody of the present invention, but is not otherwise particularly limited.

The "sample" here should be a sample that contains or has the potential to contain CSE, but is not otherwise particularly limited, and the following, for example, are examples of sample sources: body fluids such as urine, blood, plasma, serum, synovial fluid, spinal fluid, and so forth; secretions; cells such as animal cells, plant cells, and so forth; tissues; organs; and cultures of cells or microorganisms.

There are no particular limitations in the CSE detection method of the present invention on the specific method for the detection of the CSE present in a sample, but the latter can be exemplified by the ELISA method, RIA method, plaque method, agglutination reaction method, flow cytometry method, tissue staining method, western blot method, surface plasmon resonance method, etc The detection in the CSE detection method of the present invention may be a quantitative detection or a qualitative detection. When it is a quantitative detection, the CSE concentration present in a sample can be determined, for example, by constructing—using CSE standard solutions of already known concentrations—a calibration curve for the relationship between the CSE concentration and the detection result, and checking the detection result with this calibration curve for the sample of unknown CSE concentration.

The CSE detection kit of the present invention contains at least the antibody of the present invention, but is not otherwise particularly limited. The CSE detection method of the present invention can be more simply and conveniently carried out using the CSE detection kit of the present invention. Here, a "kit that contains at least the antibody of the present invention" can be exemplified by a kit that contains as a constituent component the antibody of the present invention as such (this also includes, for example, the antibody of the present invention dissolved in a solution), a kit that contains as a constituent component a solid phase on which the antibody of the present invention is immobilized, and a kit containing as a constituent component the antibody of the present invention that has been labeled with, for example, an enzyme. In addition to the antibody of the present invention, the constituent components of the CSE detection kit of the present invention may include, for example, a secondary antibody, reaction buffer, wash solution, reaction substrate, CSE standard solution, and so forth.

The method of producing the antibody of the present invention contains at least a step of carrying out an immunization using as antigen a substance in which a lipid is linked with chondroitin sulfate E, but is not otherwise particularly limited. The methods described in 1. to 6. above and the methods described in the following examples can be used for the specific method of producing the antibody.

EXAMPLES

The present invention is specifically described in the following using reference examples and examples. The present invention is not limited to or by these reference examples and examples.

(Reference Example 1) Preparation of CSE

CSE can be prepared by extraction from squid cartilage via a protease treatment and alcohol precipitation (J. Biochem. 60, 317-321 (1966)), enzymatic treatment, and column chromatography (J. Biol. Chem. 236, 983-987 (1961), J. Biol. Chem. 252, 4570-4576 (1977)).

The weight-average molecular weight, the sulfur content and E structure content of CSE prepared as the above were 14.6 kDa, 10.0% and more than 70%, respectively (the analytical methods for CSE are given below). This CSE was used as the CSE antigen.

(Reference Example 2) Analysis of the Molecular Weight and Disaccharide Composition of the CSE (1) Analysis of the Molecular Weight The molecular weight of the CSE antigen was analyzed by the gel filtration of 50 µL of a 0.2% solution of the CSE using HPLC (HLC-8220GPC, Tosoh Corporation). A train of TSKgel PWXLG4000 (0008020, 7.8 mm I.D.×30 cm, Tosoh Corporation), TSKgel PWXLG3000 (0008021, 7.8 mm I.D.×30 cm, Tosoh Corporation), and TSKgel PWXLG2500 (0008022, 7.8 mm I.D.×30 cm, Tosoh Corporation) was used as the gel filtration column. Development was carried out using 0.2 M NaCl as the mobile phase under conditions of a column temperature of 40° C. and a flow rate of 0.6 mL/min. A differential refractometer was used for CSE detection. The average molecular weight was calculated using a CS molecular weight standard product for the control. The molecular weight of the standard CS was measured by a light scattering application. Using this standard product for control, the weight-average molecular weight (Mw) and the number-average molecular weight (Mn) determined for the CSE were, respectively, 14.6 kDa and 7.7 kDa, and the molecular weight dispersity (Mw/Mn) was 1.8.

(2) Analysis of the Disaccharide Composition

For disaccharide analysis to confirm the position of substitution of the sulfate groups in the CSE antigen, the disaccharide fraction provided by digestion with C-ABC was quantitated using an HPLC postcolumn microfluorometric disaccharide analysis system (Toyoda H, et al., J. Biol. Chem. (2000) 275, 2269-2275).

The disaccharide composition was analyzed by HPLC (Waters). A reverse-phase column (Senshu Pak DOCOSIL SP100, DC-A151-SP, 1 mm ID×15 cm, Senshu Scientific Co., Ltd.) was used, and the fluorescence intensity was measured at an excitation wavelength of 346 nm and a measurement wavelength of 410 nm. For the eluent, A) DW (gradient), B) 0.2 M NaCl (gradient), C) 10 mM tetra-n-butylammonium hydrogen sulfate 12% (isocratic), and D) 50% acetonitrile 17% (isocratic) were run at a flow rate of 1.1 mL/min (Alliance 2695) and 0.5% 2-cyanoacetamide and 0.25 M sodium hydroxide were run at 0.7 mL/min (600E). Development was carried out using a column temperature condition of 55° C.

The disaccharide composition analysis gives the proportions of disaccharides having specific structures—using 100% for the amount of the identifiable unsaturated disaccharides (sum of the mol % for ΔDi-0S, ΔDi-4S, ΔDi-6S, ΔDi-2S, ΔDi-(4,6)S, ΔDi-(2,4)S, ΔDi-(2,6)S, and ΔDi-(2,4,6)S) obtained in the disaccharide analysis by enzymatic digestion—and the numerical values reflect the sulfation of the sulfated polysaccharides prior to enzymatic digestion. The unsaturated disaccharides provided by the separation and purification of enzymatic digests of CSA, CSC, CSD, DS, and HA were used as the standard substances (J. Biol. Chem. 234, 1543-1550 (1968), Anal. Biochem. 146, 327-335 (1985)).

The disaccharide composition determined using this procedure is given in Table 1 below.

TABLE 1

| sample | ΔDi- | | | | | | | | S content (%) |
|---|---|---|---|---|---|---|---|---|---|
| | 0S | 4S | 6S | 2S | (4,6)S (%) | (2,4)S | (2,6)S | (2,4,6)S | |
| CSE antigen | 6.4 | 17.5 | 5.7 | 0.0 | 70.4 | 0.0 | 0.0 | 0.0 | 10.0 |

The structures indicated by the abbreviations used above are as follows.
ΔDi-0S: ΔHexA1-3HexNAc
ΔDi-4S: ΔHexA1-3HexNAc(4S)
ΔDi-6S: ΔHexA1-3HexNAc(6S)
ΔDi-2S: ΔHexA(2S)1-3HexNAc
ΔDi-(4,6)S: ΔHexA1-3HexNAc(4S,6S)
ΔDi-(2,4)S: ΔHexA(2S) 1-3HexNAc (4S)
ΔDi-(2,6)S: ΔHexA(2S)1-3HexNAc(6S)
ΔDi-(2,4,6)S: ΔHexA(2S)1-3HexNAc(4S,6S)

In the preceding, ΔHexA represents the unsaturated uronic acid; HexNAc represents N-acetylhexosamine; and the sulfate group bonding position is given in parentheses.

(Reference Example 3) Preparation of 6-O-Desulfated CSE (de6S-CSE)

De6S-CSE was prepared by the selective desulfation of the position 6 sulfate group on the CSE obtained as described above. This procedure is described as follows. Proton formed CSE was neutralized with pyridine anhydrous to obtain the CSE pyridinium salt. 50 mg of the CSE pyridinium salt was reacted for 2 hours at 60° C. in pyridine anhydrous with [bis(triethylsilyl)acetamide] (BTSA). The reaction was stopped by the addition of distilled water to the reaction solution, and dialyzed to remove the salt. After dialysis, the solution was boiled for 30 minutes and then returned to room temperature, followed by adjusting the pH to 9.5 with 0.5 M NaOH. The re-dialyzed solution was lyophilized to obtain a powder; 40 mg was recovered.

This powder was analyzed according to the aforementioned (1) molecular weight analysis and (2) disaccharide composition analysis. The weight-average molecular weight (Mw) and the number-average molecular weight (Mn) were 12.7 kDa and 6.5 kDa, respectively, and the molecular weight dispersity (Mw/Mn) was 1.9. The disaccharide composition was 18.0% ΔDi-0S, 82.0% ΔDi-4S, 0% ΔDi-6S, 0% ΔDi-2S, 0% ΔDi-(4,6)S, 0% ΔDi-(2,4)S, 0% ΔDi-(2,6)S, and 0% ΔDi-(2,4,6)S, and the selective desulfation of the position 6 sulfate group was thus confirmed.

(Reference Example 4) Preparation of Fully Desulfated CSC (deS-CSC)

deS-CSC was prepared according to the method of carrying out desulfation by reacting CSC in methanol/acetyl chloride (Thomas G. Kantor, Maxwell Schubert. (1957) J. Am. Chem. Soc. 79, 152-153).

The CSC powder was analyzed according to the aforementioned (1) molecular weight analysis and (2) disaccharide composition analysis. The disaccharide composition of the CSC before desulfation was 1.9% ΔDi-0S, 17.8% ΔDi-4S, 68.2% ΔDi-6S, 0% ΔDi-2S, 1.3% ΔDi-(4,6)S, 0% ΔDi-(2,4)S, 10.8% ΔDi-(2,6)S, and 0% ΔDi-(2,4,6)S. Upon passage through the aforementioned preparative procedure, the weight-average molecular weight (Mw) and number-average molecular weight (Mn) were 5.9 kDa and 3.9 kDa, respectively, and the molecular weight dispersity (Mw/Mn) was 1.5. The disaccharide composition was 91.2% ΔDi-0S, 0% ΔDi-4S, 8.7% ΔDi-6S, 0% ΔDi-2S, 0% ΔDi-(4,6)S, 0% ΔDi-(2,4)S, 0% ΔDi-(2,6)S, and 0% ΔDi-(2,4,6)S, which confirmed that desulfation had occurred.

(Reference Example 5) Preparation of Biotin-Labeled Gags 5 mg of the particular GAG (CSE, CSA, CSB, CSC, CSD, deS-CSC, Hep, HS, HPN, KS, HA, de6S-CSE) was dissolved in 1 mL of 2 M $NH_4Cl$ solution. 50 mg of $NaCNBH_3$ was added to the resultant solution and a reaction was run for 48 hours at 70° C. Another 25 mg of $NaCNBH_3$ was added and a reaction was run for 48 hours at 70° C. In order to remove the salt from the reaction solution, dialysis was carried out overnight using a dialysis membrane (MWCO 12,000 to 14,000). After the dialysis, the solution was lyophilized to recover a powder.

The lyophilized powder was dissolved in 450 μL PBS; 50 μL of a biotin solution (biotin 10 mg/222 μL in DMF) was added and incubated for 30 minutes at room temperature. After the incubation, dialysis was performed overnight using a dialysis membrane (MWCO 12,000 to 14,000) and the resulting solution was lyophilized to recover the biotin-labeled GAG (CSE, CSA, CSB, CSC, CSD, deS-CSC, Hep, HS, HPN, KS, HA, de6S-CSE) as a powder.

Example 1

Preparation of CSE Antigen
(1) Preparation of CSE-Tetrabutylammonium Salt ("CSE-but$_4$N$^+$ Salt" in the Following)

1.0 g of the CSE prepared in Reference Example 1 was dissolved in 50 mL of distilled water and was applied to a Dowex 50W-X8-H$^+$ form (217514-500 g, SIGMA) column (2.5 cm ϕ×6.5 cm). CSE prepared sodium-free was recovered as the acidic fraction of the eluted solution. To this was added tetrabutylammonium (10% in water) (T0955, Tokyo Chemical Industry Co., Ltd.) and the pH was adjusted from acidity to neutrality (pH 7.15). The solution was lyophilized for 3 days at room temperature and 1.85 g of the CSE-But$_4$N$^+$ salt was recovered as a dry powder.

(2) Preparation of CSE-PE 1.85 g of the CSE-But$_4$N$^+$ dry powder was dissolved in 25 mL of dehydrated methanol and 104 mg (150 μmol) of PE (163-161193, Wako) was added. After stirring for 1 hour at 50° C. under an argon gas atmosphere, 36 mg of trimethylamine borane (T1181, Tokyo Chemical Industry Co., Ltd.) was added and stirring at 50° C. was continued for 24 hours. In addition, the reaction was carried out at 50° C. by adding 36 mg of trimethylamine borane divided into two portions at 24-hour intervals to obtain a CSE-PE reaction solution.

(3) Purification of CSE-PE

The reaction solution described in (2) above was concentrated under reduced pressure and methanol was added and concentration under reduced pressure was repeated and the trimethylamine borane was thus removed as the azeotrope with methanol. 40 mL of 0.2 M sodium acetate was added to the residue; stirring was carried out for 2 hours at room temperature; and the insolubles were removed by centrifugal separation (6000 rpm, 30 minutes). Three-fold (120 mL) sodium acetate-saturated ethanol was added to the supernatant to precipitate the target substance. The obtained precipitate was dissolved in distilled water and 0.83 g of a powder was then recovered by lyophilization.

0.7 g of the 0.8 g of powder was dissolved in 25 mL of water and 25 mL of methanol; 20 g of Cellufine Butyl (19905, JNC Corporation) gel was added; and, while the suspension was being stirred, 10 mL of 1 M NaCl was added dropwise and stirring was performed for 2 hours at 4° C. The suspension was then filled into a column (2.5 cm ϕ×25 cm).

The solution on the column was drained; washing with 200 mL 0.2 M NaCl was performed; and elution was carried out using 50 mL distilled water and 200 mL of a 30% (v/v) methanol-distilled water mixture (methanol-eluted fraction). The methanol-eluted fraction was dried to solidification by concentration under reduced pressure and was then redissolved in distillated water; this was followed by running water dialysis with a dialysis membrane MWCO of 12,000 to 14,000 and then lyophilization to recover a powder. The weight of the recovered CSE-PE powder was 50 mg.

Example 2

Acquisition of Hybridoma that Produces CSE-Reactive Monoclonal Antibody (1) Preparation of Antigen for Immunization The CSE-PE prepared in Example 1 was dissolved in PBS to give a final concentration of 2 mg/mL, and, after ultrasound treatment, the final concentration was brought to 0.1 mg/mL and heated to 37° C. To this was added 1136 µL of a solution prepared by the suspension in advance at 1 mg/mL of acid-treated *Salmonella minnesota* cell membrane in PBS, followed by standing for 10 minutes at 37° C. This mixed solution was dispensed into 200 µL, and stored at −20° C.

(2) Mice Immunization

The dispensed solution produced in (1) above was administered at 200 µL, each time via tail vein injection to three C3H/HeN mice (age: 6 weeks) on day 0, 4, 7, 11, 21, and 25. To confirm the antibody titer by ELISA, retro-orbital blood collection was performed on day 29; this was held overnight at 4° C. and then centrifuged for 10 minutes at 5000 rpm, after which the serum was recovered and stored at −80° C.

(3) Measurement of the Antibody Reaction by the ELISA Method

The CSE-PE prepared in Example 1 was dissolved at 2.5 µg/50 µL, in 70% EtOH, and this solution was added at 50 µL/well to an F-bottom 96-well microtiter plates (3355, Thermo Fisher Scientific Inc.).

CSE-PE was immobilized by drying under reduced pressure. And 200 µL/well of 1% human serum albumin-PBS was added as blocking solution and holding for 1 hour at room temperature was carried out. The blocking solution was removed by washing one time with PBS at 200 µL/well.

The mice serum produced as described in (1) above and diluted with PBS were added at 50 µL/well and incubated for 1 hour at room temperature. The serum was removed and washed three times with PBS at 200 µL/well. For the secondary antibody, a horseradish peroxidase-labeled goat anti-mouse IgG+IgM diluted to 2000λ with 1% human serum albumin-PBS was added at 50 µL/well and incubated for 1 hour at room temperature. After removal of the secondary antibody solution, washing was performed three times with PBS at 200 µL/well.

For color development and measurement, a color development solution [solution prepared by dissolving 2 mg o-phenylenediamine in 5 mL of 80 mM citric acid-phosphate buffer solution (pH 5.6) followed by the addition of 2 µL of 30% aqueous hydrogen peroxide] was added at 100 µL/well. Holding was carried out under light exclusion, and, once color development was observed, color development was stopped with 1 N HCl solution at 100 µL/well. The absorbance was measured with a microplate reader (SK603) that carried out measurement at a measurement wavelength of $\lambda_1$=492 nm and a control wavelength of $\lambda_2$=630 nm.

Immunization by the antigen was confirmed because the sera from the three mice reacted with the CSE-PE in a concentration dependent manner.

(4) Culture of PAI Cells Derived from Mouse Myeloma Cells

PAI cells (JCRB Cell Bank, JCRB0113) were cultured at 37° C. under 5% $CO_2$ on 10% FBS-RPMI [contained final medium concentrations of 10% FBS, 1% PSG, 10 mM HEPES, and 1 mM sodium pyruvate].

(5) Preparation of Mice Spleen Cells

The spleen was aseptically removed from the mouse on day 32 after the start of immunization (7 days after the final immunization) and the spleen was minced in a petri dish that contained 10% FBS-RPMI medium. This was centrifuged for 5 minutes at 1300 rpm and then resuspended in 10% FBS-RPMI medium and the tissue in the suspension was removed with a cell strainer. The precipitation recovered by centrifugation for 5 minutes at 1300 rpm was resuspended in 20 mL of 10% FBS-RPMI medium to recover the spleen cells.

(6) Preparation of Hybridomas

The PAI cells was fused with spleen cells prepared as described above at a ratio of 1:5 cell/cell using polyethylene glycol #4000. 10% FBS-RPMI medium supplemented with HAT Supplement (Gibco) at a 100× dilution was used for the cell fusion medium. Culture was performed for 10 to 14 days on two 96-well plates per mouse until the appearance of HAT-resistant colonies could be observed.

Fast-growing colonies with a positive culture supernatant were cultured on 6-well plates in order to change the well surface area. Four rounds of screening tests with measurement of the antibody titer were performed up to the E-well plates.

(7) Cloning

The hybridoma cells which the culture supernatant was positive in (6) above were cloned by the limiting dilution method. CM-B cloning medium (410022517, EIDIA Co., Ltd.) was used in this cloning procedure. Dilution was performed to bring the number of cells to 1/well (5.0 cells/mL) and 0.5/well (2.5 cells/mL), respectively; seeding to 96-well microplates was carried out; and culturing was carried out for 10 to 14 days on two 96-well plates per clone. Positive clones were selected through four rounds of screening tests as in (5) above.

A second cloning procedure was then run using the clones obtained by the primary cloning. Positive clones were selected by the same procedure as described above.

(8) Hybridoma Selection

The clones selected according to (7) above were evaluated for their specificity for CSE and two clones were obtained. These two clones were respectively designated E-12C and E-18H. These hybridoma clones were deposited on Feb. 26, 2014 (deposition date) with the NITE Patent Microorganisms Depositary (NPMD) and were given accession numbers NITE P-01809 and NITE P-01808, respectively. In addition, these were transferred to international depositions under the Budapest Treaty on Feb. 17, 2015 (Accession numbers NITE BP-01809 and NITE BP-01808).

Example 3

Characteristics of the Monoclonal Antibodies (1) Monoclonal Antibody Production

The CSE-reactive monoclonal antibodies (culture supernatant) were obtained by culturing the aforementioned hybridomas and removing the cells from the culture supernatants by centrifugal separation. The E-12C antibody was obtained from the E-12C hybridoma and the E-18H antibody was obtained from the E-18H hybridoma.

(2) ELISA Test with Various GAGs

The reactivities of the E-12C antibody and the E-18H antibody for various GAGs (CSE, CSA, CSB, CSC, CSD, deS-CSC, Hep, HS, HPN, KS, HA, and de6S-CSE) were investigated by ELISA using plates immobilized biotin-labeled GAG. The following were used: CSE derived from squid, CSA derived from whale, CSB derived from porcine, CSC derived from shark, CSD derived from shark, Hep derived from bovine, HS derived from porcine, HPN from $E.$ $coli$ strain K5, KS derived from shark, and HA derived from chicken. The molecular weight, dispersity value, and sulfur content of the various GAGs used are given in Table 2 below.

TABLE 2

| GAG | Mw (kDa) | Mw/Mn | S content (%) |
|---|---|---|---|
| CSA | 16.9 | 1.2 | 6.8 |
| CSB | 16.4 | 1.0 | 7.0 |
| CSC | 42.1 | 1.5 | 7.4 |
| CSD | 31.7 | 1.1 | 8.1 |
| CSE | 14.6 | 1.8 | 10.0 |
| de6S-CSE | 12.7 | 1.9 | 5.7 |
| deS-CSC | 7.5 | 1.3 | 0.6 |
| Hep | 8.2 | 1.3 | 15.5 |
| HS | 17.8 | 1.3 | — |
| HPN | 40.8 | 1.3 | 0 |
| KS | 12.9 | 1.2 | — |
| HA | 18.7 | 1.6 | 0 |

—: not measured

1 μg/mL of the particular biotin-labeled GAG diluted with PBS were immobilized onto BioBind Strip Assembly (95029 293, Thermo Fisher Scientific Inc.), which is a streptavidin-coated plate, by holding for 1 hour at room temperature. For the negative control and the blank, a biotin solution and PBS at the same concentrations were similarly added to the plate at 50 μL/well each.

Figure 1:
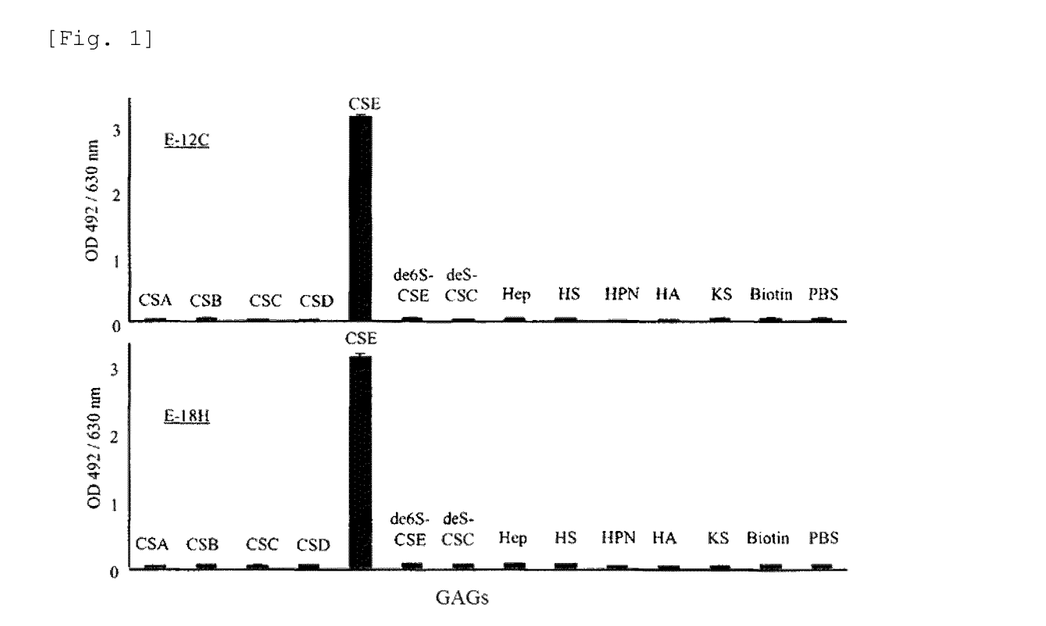
FIG. 1 is a diagram that shows the reactivity of the E-12C antibody and E-18H antibody with various GAGs.

After removal of the solution used for immobilizing, 1% human serum albumin-PBS was added as a blocking solution at 200 μL/well followed by holding for 1 hour at room temperature. The blocking solution was then removed followed by washing once with PBS at 200 μL/well, the addition of 50 μL/well of the culture supernatant, and reacting for 1 hour at room temperature. In the procedure from and after the secondary antibody, the absorbance was measured by the same method as for measurement of the antibody reaction by the ELISA method as described in (3) in Example 2 (FIG. 1). Assuming that the reactivity (absorbance value) of the antibody to CSE was setted 100%, the relative reactivity (%) between the antibody and the particular solid-phase substance was calculated from the obtained absorbance value. The results are given in Table 3 below.

TABLE 3

| solid-phased substance | reactivity (%) E-12C | reactivity (%) E-18H |
|---|---|---|
| CSA | 0.8 | 1.0 |
| CSB | 1.3 | 1.4 |
| CSC | 0.9 | 1.1 |
| CSD | 0.8 | 1.2 |
| CSE | 100 | 100 |
| de6S-CSE | 1.4 | 1.8 |
| deS-CSC | 1.0 | 1.6 |
| Hep | 1.4 | 1.7 |
| HS | 1.2 | 1.7 |
| HPN | 0.5 | 0.8 |
| HA | 0.7 | 1.1 |
| KS | 1.6 | 1.0 |
| biotin | 1.4 | 1.6 |
| PBS | 1.4 | 1.4 |

The reactivity of the antibodies E-12C and E-18H with CSE were both at least 98% that deducted the value of the negative control from the value of CSE. Thus the E-12C antibody and the E-18H antibody were both strongly reactive with CSE.

The absorbance of GAGs except CSE (CSA, CSB, CSC, CSD, Hep, HS, HPN, KS, HA, deS-CSC, and de6S-CSE) was about the same as the absorbance of the blank and negative control of PBS and solid-phased biotin (FIG. 1). The reactivity of these antibodies with GAGs except CSE were less than 0.5% that deducted the value of the negative control from the value of the GAGs. This demonstrated that the E-12C antibody and E-18H antibody both did not react with non-CSE GAG and did specifically react with CSE.

Example 4

Measurement of Antibody Subtype

The subtype was determined for the E-12C antibody and E-18H antibody using an IsoQuick™ Kit for Mouse Monoclonal Antibody Isotyping (ISOQ5, Sigma) and IsoQuick™ Strips for Mouse Monoclonal Antibody Isotyping (i9410-25EA, Sigma).

The end of the IsoQuick kit was immersed for 5 minutes in the E-12C antibody or E-18H antibody (culture supernatant) obtained according to (1) in Example 3 and was finished when a band could be confirmed. The type to which the antibodies belonged were determined from the position of the band that appeared. These results were that the E-12C antibody and E-18H antibody were both a monoband of IgM and the L chain was the κ chain.

Example 5

Production of a CSE Detection Kit

A CSE detection kit constituted of the following was produced.

1. monoclonal antibody obtained according to (1) in Example 3

2. secondary antibody (horseradish peroxidase-labeled goat anti-mouse IgG+IgM)

3. set for preparation of a color development solution at use time (80 mM citric acid-phosphate buffer solution (pH 5.6), o-phenylenediamine, 30% aqueous hydrogen peroxide)

4. solution for stopping reaction (1 N HCl)

Example 6

Reactivity of the E-12C Antibody and E-18H Antibody with Sulfated CSA and Sulfated CSB (1) Preparation of Sulfated CSA and Sulfated CSB 100 mg of CSA was dissolved in 50 mL of distilled water and this was applied to Diaion cation exchange resin (PK220, Mitsubishi Chemical Corporation) (2.5 cm φ×6.5 cm). CSA prepared sodium-free was recovered as the acidic fraction of the eluted solution. Tetrabutylamine (TBA) was added to this accumulated effluent and the pH was adjusted from acidity to neutrality. The solution was lyophilized at room temperature to obtain the CSA-TBA salt.

The CSA-TBA salt was dissolved in a solvent prepared by mixing formamide/dimethylformamide at 1:4 and the sulfur reagent sulfur trioxide/pyridine complex was added. The amount of addition of the sulfur reagent was 8 equivalents per disaccharide unit. After the sulfated reaction, distilled water was added to the solution to stop the reaction and neutralization was carried out with sodium hydroxide. This solution was dialyzed overnight with a dialysis membrane MWCO from 12,000 to 14,000, followed by lyophilization to obtain 160 mg of sulfated CSA. Proceeding in this manner, sulfated CSA can be prepared by the introduction of the sulfate group at position 6 of the GalNAc of CSA (Carbohydr. Res. 158, 183-190 (1986)). 160 mg of sulfated CSB was obtained by sulfation of CSB in the same manner.

(2) Analysis of the Molecular Weight and Disaccharide Composition of the Sulfated CSA and Sulfated CSB The analyses were performed by the methods described in "(1) Analysis of the molecular weight, (2) Analysis of the disaccharide composition of (Reference Example 2)". The results are given in Table 4. In the table, CSA-8S refers to the sulfated CSA provided by the addition of 8 equivalents of the sulfur reagent and CSB-8S similarly refers to the sulfated CSB provided by the addition of 8 equivalents of the sulfur reagent.

TABLE 4

| GAG | MW (kDa) | ΔDi-0S | 4S | 6S | 2S | (4,6)S (%) | (2,4)S | (2,6)S | (2,4,6)S | S content (%) |
|---|---|---|---|---|---|---|---|---|---|---|
| CSA | 16.9 | 2.2 | 97.8 | 0 | 0 | 0 | 0 | 0 | 0 | 6.8 |
| CSA-8S | 20.1 | 0.1 | 3.6 | 27.6 | 0 | 59.4 | 0 | 4.7 | 4.6 | 10.6 |
| CSB | 16.4 | 5.9 | 75.6 | 8.4 | 0 | 1.1 | 8.0 | 1.0 | 0 | 7.0 |
| CSB-8S | 20.8 | 2.5 | 8.0 | 8.9 | 0 | 66.0 | 2.9 | 1.7 | 10.0 | 10.9 |

The structures indicated by the abbreviations used above are as follows.

ΔDi-0S: ΔHexA1-3HexNAc

ΔDi-4S: ΔHexA1-3HexNAc(4S)

ΔDi-6S: ΔHexA1-3HexNAc(6S)

ΔDi-2S: ΔHexA(2S)1-3HexNAc

ΔDi-(4,6)S: ΔHexA1-3HexNAc(4S,6S)

ΔDi-(2,4)S: ΔHexA(2S)1-3HexNAc(4S)

ΔDi-(2,6)S: ΔHexA(2S)1-3HexNAc(6S)

ΔDi-(2,4,6)S: ΔHexA(2S)1-3HexNAc(4S,6S)

In the preceding, ΔHexA represents the unsaturated uronic acid; HexNAc represents N-acetylhexosamine; and the sulfate group bonding position is given in parentheses.

The ΔDi-(4,6)S structure content rate was 59.4% in the CSA-8S provided by sulfation of the 6 position in CSA, which has the basic disaccharide unit [GlcAβ1-3GalNAc(4S)]. This confirmed the preparation of a sulfated CSA that contained mainly the basic disaccharide unit of CSE [GlcAβ1-3GalNAc(4S,6S)] (also referred to as the E structure in the following). In addition, the ΔDi-(4,6)S structure content rate was 66.0% in the CSB-8S provided by sulfation of the 6 position in CSB, which has the basic disaccharide unit [IdoAβ1-3GalNAc(4S)]. This confirmed the preparation of a sulfated CSB that contained mainly the basic disaccharide unit [IdoAβ1-3GalNAc(4S,6S)].

The thusly prepared sulfated CSA and sulfated CSB were biotinylated by the method described in "Preparation of biotin-labeled GAGs of Reference Example 5" in order to prepare biotinylated sulfated CSA and biotinylated sulfated CSB.

Figure 2:
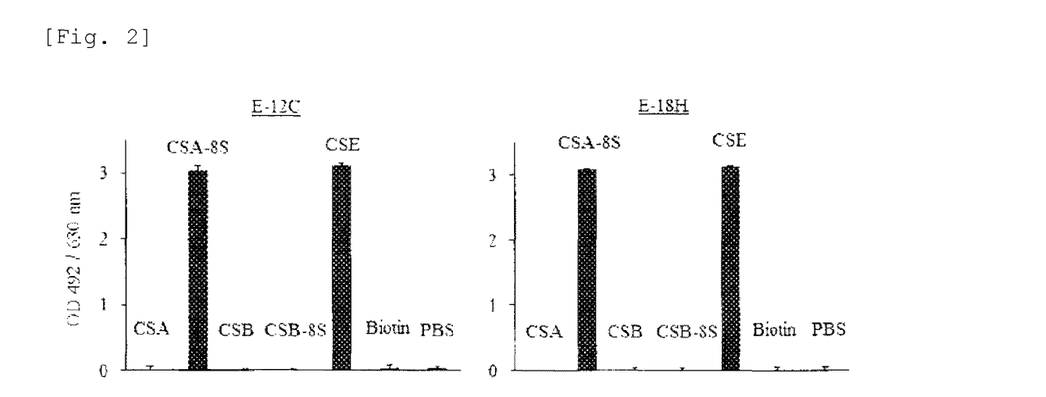
FIG. 2 is a diagram that shows the reactivity of the E-12C antibody and E-18H antibody with several GAGs, e.g., sulfated CSA and sulfated CSB.

Testing was carried out by the method described in "Characteristics of the monoclonal antibodies of Example 3" in order to evaluate the reactivity of the E-12C antibody and E-18H antibody for the sulfated CSA and sulfated CSB using ELISA. The results are given in Table 5 and FIG. 2.

TABLE 5

| immobilized substance | reactivity (%) E-12C | reactivity (%) E-18H |
|---|---|---|
| CSA | 0.9 | 0.2 |
| sulfated CSA | 97.8 | 98.9 |
| CSB | 0.6 | 0.7 |
| sulfated CSB | 0.6 | 0.7 |
| CSE | 100 | 100 |
| biotin | 1.3 | 1.2 |
| PBS | 1.2 | 1.0 |

The reactivity of the antibodies E-12C and E-18H with the sulfated CSA were both at least 96% that deducted the value of the negative control from the value of the sulfated CSA, and this reactivity was about equal to that for CSE. The E-12C antibody and the E-18H antibody were both strongly reactive with sulfated CSA.

It was thus confirmed that the E-12C antibody and E-18H antibody were reactive not only with squid-derived CSE, but also with CSE (sulfated CSA) that chemically synthesized from CSA.

The absorbance in the case of CSA, CSB, and sulfated CSB was about the same as the absorbance for the blank and negative control. This confirmed that the E-12C antibody and E-18H antibody did not react with CSA, CSB, or sulfated CSB.

Example 7

Interaction Analysis by the Surface Plasmon Resonance Method
(1) Immobilization of the Ligand GAG by the Amine Coupling Method The negatively charged carboxyl group is present in the linear dextran coated on the surface of a CM5 sensor chip. The carboxyl group was activated with NHS (N-hydroxysuccinimide), and streptavidin dissolved at 50 μg/mL in 10 mM acetate buffer (pH 5.5) was immobilized. The active NHS group remaining after immobilization was blocked with ethanolamine. After blocking, the biotinylated GAGs that will function as the ligand were added so as to obtain an immobilized amount of at least 50 RU (resonance units). For the reference cell, biotin was also immobilized in the same manner to provide a negative control cell. PBS was supplied at a flow rate of 10 μL/min as the running buffer, and the analysis was performed at a temperature condition of 25° C.
(2) Analysis of the Interaction The interaction was analyzed using as the analyte the culture supernatant for the E-12C antibody or E-18H antibody after passage across a 0.22-μm filter. The antibody culture supernatants were prepared by dilution with PBS so as to be 2 nM as the IgM concentration. Interaction with the ligand was carried out by injection at a flow rate of 20 μL/min. The sensorgram provided by subtracting the response for the reference cell was displayed, and the case in which a response was absent was regarded as no detection (ND). When an analyzable response was obtained, the equilibrium dissociation constant (KD) was calculated from the values of the association rate constant (ka) and dissociation rate constant (kd) using a 1:1 binding model. The value of KD can be determined using kd/ka.
(3) Preparation of CSEs with Different Molecular Weights CSEs with different molecular weights can be prepared by enzymatic treatment and column chromatography (J. Biol. Chem. 236, 983-987 (1961), J. Biol. Chem. 252, 4570-4576 (1977)). CSEs having five different molecular weights were prepared with reference to this literature.

The prepared five CSEs having different molecular weights were analyzed. The analysis was carried out using the methods described in "(1) Analysis of the molecular weight, (2) Analysis of the disaccharide composition of Reference Example 2". The results are shown in Table 6.

The structures indicated by the abbreviations used above are as follows.
ΔDi-0S: ΔHexA1-3HexNAc
ΔDi-4S: ΔHexA1-3HexNAc(4S)
ΔDi-6S: ΔHexA1-3HexNAc(6S)
ΔDi-2S: ΔHexA(2S)1-3HexNAc
ΔDi-(4,6): ΔHexA1-3HexNAc(4S,6S)
ΔDi-(2,4): ΔHexA(2S)1-3HexNAc(4S)
ΔDi-(2,6): ΔHexA(2S)1-3HexNAc(6S)
ΔDi-(2,4,6)S: ΔHexA(2S)1-3HexNAc(4S,6S)

In the preceding, ΔHexA represents the unsaturated uronic acid; HexNAc represents N-acetylhexosamine; and the sulfate group bonding position is given in parentheses.

The CSE having a weight-average molecular weight (Mw) of 68.0 kDa and an E structure content of 61.4% was designated CSE-68K. The CSE having a weight-average molecular weight (Mw) of 56.7 kDa and an E structure content of 61.0% was designated CSE-56K. The CSE having a weight-average molecular weight (Mw) of 24.1 kDa and an E structure content of 63.0% was designated CSE-24K. The CSE having a weight-average molecular weight (Mw) of 14.6 kDa and an E structure content of 70.4% was designated CSE-14K. This CSE-14K is the same as the CSE used for the immunizing antigen in antibody production. The CSE having a weight-average molecular weight (Mw) of 8.7 kDa and an E structure content of 66.7% was designated CSE-8K. These five CSEs were used.
(4) Interaction Analysis on the CSEs with Different Molecular Weights The five CSEs described in Table 6 above and de6S-CSE were immobilized on the sensor chips and submitted to interaction analysis. Testing was performed by the methods described in "(1) Immobilization of the ligand by the amine coupling method, (2) Measurement of the interaction of Example 7". The results are given in table 7.

TABLE 7

| antibody | ligand CSE | MW (kDa) | ka (1/Ms) | kd (1/s) | KD (M) |
|---|---|---|---|---|---|
| E-12C | CSE-68K | 68.0 | $3.5 \times 10^7$ | $5.5 \times 10^{-4}$ | $1.7 \times 10^{-11}$ |
|  | CSE-56K | 56.7 | $3.0 \times 10^7$ | $1.0 \times 10^{-3}$ | $3.4 \times 10^{-11}$ |
|  | CSE-24K | 24.1 | $3.8 \times 10^6$ | $8.2 \times 10^{-4}$ | $2.3 \times 10^{-10}$ |
|  | CSE-14K | 14.6 | $5.7 \times 10^6$ | $2.0 \times 10^{-3}$ | $3.6 \times 10^{-10}$ |
|  | CSE-8K | 8.7 | $3.7 \times 10^6$ | $1.4 \times 10^{-3}$ | $3.7 \times 10^{-10}$ |
| E-18H | CSE-68K | 68.0 | $2.9 \times 10^7$ | $3.8 \times 10^{-4}$ | $1.5 \times 10^{-11}$ |
|  | CSE-56K | 56.7 | $3.4 \times 10^7$ | $8.5 \times 10^{-4}$ | $2.5 \times 10^{-11}$ |
|  | CSE-24K | 24.1 | $6.3 \times 10^6$ | $7.6 \times 10^{-4}$ | $1.2 \times 10^{-10}$ |
|  | CSE-14K | 14.6 | $7.3 \times 10^6$ | $1.8 \times 10^{-3}$ | $2.5 \times 10^{-10}$ |
|  | CSE-8K | 8.7 | $4.3 \times 10^6$ | $1.2 \times 10^{-3}$ | $2.9 \times 10^{-10}$ |

TABLE 6

| CSE | MW (kDa) | ΔDi- 0S | 4S | 6S | 2S | (4,6)S (%) | (2,4)S | (2,6)S | (2,4,6)S | S content (%) |
|---|---|---|---|---|---|---|---|---|---|---|
| CSE-68K | 68.0 | 9.3 | 23.8 | 5.5 | 0.0 | 61.4 | 0.0 | 0.0 | 0.0 | 9.3 |
| CSE-56K | 56.7 | 8.0 | 25.2 | 5.8 | 0.0 | 61.0 | 0.0 | 0.0 | 0.0 | 9.4 |
| CSE 24K | 24.1 | 8.1 | 23.1 | 5.7 | 0.0 | 63.0 | 0.0 | 0.0 | 0.0 | 9.5 |
| CSE 14K | 14.6 | 6.4 | 17.5 | 5.7 | 0.0 | 70.4 | 0.0 | 0.0 | 0.0 | 10.0 |
| CSE-8K | 8.7 | 9.3 | 19.5 | 4.5 | 0.0 | 66.7 | 0.0 | 0.0 | 0.0 | 9.6 |

The KD value between CSE-14K and the E-12C antibody and between CSE-14K and the E-18H antibody was, respectively, $3.6 \times 10^{-10}$ (M) and $2.5 \times 10^{-10}$ (M), and a strong interaction was thus demonstrated for the antigen-antibody reaction. No reactivity was detected (ND) between the E-12C antibody or E-18H antibody and de6S-CSE, which was provided by the selective desulfation of the 6 position of the CSE antigen.

The KD value between the E-12C antibody and CSE-68K was $1.7 \times 10^{-11}$ (M); for CSE-56K it was $3.4 \times 10^{-11}$ (M); for CSE-24K it was $2.3 \times 10^{-10}$ (M); for CSE-14K it was $3.6 \times 10^{10}$ (M); and for CSE-8K it was $3.7 \times 10^{-10}$ (M). The KD value between the E-18H antibody and CSE-68K was $1.5 \times 10^{-11}$ (M); for CSE-56K it was $2.5 \times 10^{-11}$ (M); for CSE-24K it was $1.2 \times 10{-10}$ (M); for CSE-14K it was $2.6 \times 10^{-1 \circ}$ (M); and for CSE-8K it was $2.9 \times 10^{-10}$ (M). All of these KD values were equal to or less than $1 \times 10^{-9}$ (M), and the occurrence of a strong interaction was thus confirmed.

(5) Analysis of the Interaction with Sulfated CSAs with Different E Structure Contents Reactions were carried out by adding 2, 4, or 6 equivalents of the sulfur trioxide/pyridine complex sulfating agent to the CSA-TBA salt. In the subsequent procedure, preparation was carried out according to the method described for the preparation of sulfated CSA and sulfated CSB in Example 6(1). Analysis of the molecular weight and disaccharide composition of the prepared sulfated CSAs was performed by the methods described in the (1) Analysis of the molecular weight and (2) Analysis of the disaccharide composition in Reference Example 2. The results are given in Table 8.

by the addition of 6 equivalents is designated CSA-6S. The E structure content rate of CSA-2S was 14.1%; the E structure content rate of CSA-4S was 32.7%; and the E structure content rate of CSA-6S was 45.9%; and the E structure was thus produced in correspondence to the equivalents of sulfating agent added. These results are given in Table 9 along with the results for CSA, CSA-8S, CSB, and CSB-8S given in "Table 4 of Example 6".

TABLE 9

| antibody | ligand GAG | E structure content (%) | ka (1/Ms) | kd (1/s) | KD (M) |
|---|---|---|---|---|---|
| E-12C | CSA | 0.6 | ND | ND | ND |
| | CSA-2S | 14.1 | ND | ND | ND |
| | CSA-4S | 32.7 | $8.0 \times 10^5$ | $8.4 \times 10^{-3}$ | $1.0 \times 10^{-8}$ |
| | CSA-6S | 45.9 | $4.0 \times 10^5$ | $1.4 \times 10^{-3}$ | $3.5 \times 10^{-9}$ |
| | CSA-8S | 59.4 | $1.0 \times 10^6$ | $7.4 \times 10^{-4}$ | $7.8 \times 10^{-10}$ |
| E-18H | CSA | 0.6 | ND | ND | ND |
| | CSA-2S | 14.1 | ND | ND | ND |
| | CSA-4S | 32.7 | $9.6 \times 10^5$ | $9.0 \times 10^{-3}$ | $9.4 \times 10^{-9}$ |
| | CSA-6S | 45.9 | $7.1 \times 10^5$ | $1.2 \times 10^{-3}$ | $1.8 \times 10^{-9}$ |
| | CSA-8S | 59.4 | $1.4 \times 10^6$ | $6.0 \times 10^{-3}$ | $4.3 \times 10^{-10}$ |

Reactivity was not detected between the E-12C antibody and CSA and was not detected between the E-12C antibody and CSA-2S. The KD value between the E-12C antibody and CSA-4S was $1.0 \times 10^{-8}$ (M) and was $3.5 \times 10^{-9}$ (M) for CSA-6S and was $7.8 \times 10^{-10}$ (M) for CSA-8S. Reactivity was not detected between the E-18H antibody and CSA and was not detected between the E-18H antibody and CSA-2S. The

TABLE 8

| | | | | | ΔDi- | | | | |
|---|---|---|---|---|---|---|---|---|---|
| GAG | MW (kDa) | 0S | 4S | 6S | 2S | (4,6)S (%) | (2,4)S | (2,6)S | (2,4,6)S | S content (%) |
| CSA | 16.9 | 2.2 | 97.8 | 0 | 0 | 0 | 0 | 0 | 0 | 6.8 |
| CSA-2S | 19.0 | 1.4 | 50.1 | 32.0 | 0 | 14.1 | 0 | 2.3 | 0.1 | 8.0 |
| CSA-4S | 19.6 | 0.8 | 34.4 | 28.4 | 0 | 32.7 | 0 | 3.1 | 0.6 | 8.7 |
| CSA-6S | 18.0 | 0.8 | 15.2 | 30.2 | 0 | 45.9 | 0 | 4.7 | 3.2 | 9.7 |
| CSA-8S | 20.1 | 0.1 | 3.6 | 27.6 | 0 | 59.4 | 0 | 4.7 | 4.6 | 10.5 |
| CSB | 16.4 | 5.9 | 75.6 | 8.4 | 0 | 1.1 | 8.0 | 1.0 | 0 | 7.0 |
| CSB-8S | 20.8 | 2.5 | 8.0 | 8.9 | 0 | 66.0 | 2.9 | 1.7 | 10.0 | 10.9 |

The structures indicated by the abbreviations used above are as follows.
ΔDi-0S: ΔHexA1-3HexNAc
ΔDi-4S: ΔHexA1-3HexNAc(4S)
ΔDi-6S: ΔHexA1-3HexNAc(6S)
ΔDi-2S: ΔHexA(2S)1-3HexNAc
ΔDi-(4,6): ΔHexA1-3HexNAc(4S,6S)
ΔDi-(2,4): ΔHexA(2S)1-3HexNAc(4S)
ΔDi-(2,6): ΔHexA(2S)1-3HexNAc(6S)
ΔDi-(2,4,6)S: ΔHexA(2S)1-3HexNAc(4S,6S)

In the preceding, ΔHexA represents the unsaturated uronic acid; HexNAc represents N-acetylhexosamine; and the sulfate group bonding position is given in parentheses.

The product prepared by the addition of 2 equivalents of the sulfur trioxide/pyridine complex sulfating agent is designated CSA-2S; the product produced by the addition of 4 equivalents is designated CSA-4S; and the product prepared KD value between the E-18H antibody and CSA-4S was $9.4 \times 10^{-9}$ (M) and was $1.8 \times 10^9$ (M) for CSA-6S and was $4.3 \times 10^{-10}$ (M) for CSA-8S.

Reactivity by the E-12C antibody was not detected for either CSB or sulfated CSB, and reactivity by the E-18H antibody was not detected for either CSB or sulfated CSB.

Example 8

The tissue staining behavior of the anti-CSE antibodies was investigated as follows.

(1) Immunohistostaining on Frozen Sections

Squid cartilage was converted into small pieces; the tissue fragments were embedded in Tissue-Tek O.C.T. Compound (Sakura Finetek Japan Co., Ltd.); freezing was performed with liquid nitrogen; and frozen sections were prepared.

The prepared sections were fixed for 10 minutes at room temperature with 10% neutral buffered formalin solution followed by washing twice with 50 mmol/L tris-hydrochloric acid buffer.

Washing was performed three times with 0.01 mol/L phosphate-buffered saline and blocking was carried out for 10 minutes at room temperature using 0.3% hydrogen peroxide in methanol. Washing was performed three times with 0.01 mol/L phosphate-buffered saline and blocking was carried out for 60 minutes at room temperature using 0.1% casein solution (Wako Pure Chemical Industries, Ltd.).

The anti-CSE antibody (E-12C or E-18H), diluted to 12 μg/mL with 0.1% casein solution, was reacted for 60 minutes at 37° C. Mouse IgM (Sigma) was used here for the negative control.

Washing was performed three times with 0.01 mol/L phosphate-buffered saline followed by reaction for 10 minutes at room temperature with biotin-labeled anti-mouse IgG+IgA+IgM antibody (Histofine SAB-PO(M) Kit, Nichirei Biosciences Inc.). Washing was performed three times with 0.01 mol/L phosphate-buffered saline followed by reaction for 5 minutes at room temperature with peroxidase-labeled streptavidin (Histofine SAB-PO(M) Kit, Nichirei Biosciences Inc.). Washing was performed three times with 0.01 mol/L phosphate-buffered saline followed by immersion for 5 minutes in 50 mmol/L tris-hydrochloric acid buffer and then staining for 5 minutes with DAB (Dojindo Laboratories). After washing with ultrapure water, dehydration, clearing, and mounting were carried out by common methods.

Figure 3:
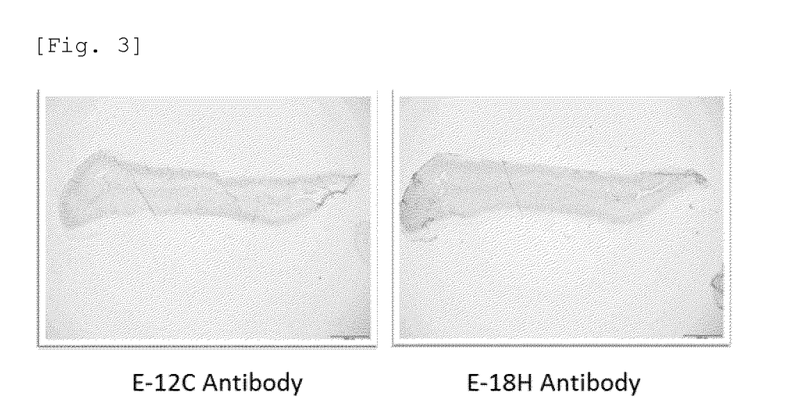
FIG. 3 is a diagram (photograph) of the staining of frozen tissue sections using the E-12C antibody and E-18H antibody.

The obtained stained images are given in FIG. 3. Staining was seen with both the E-12C antibody and the E-18H antibody. Staining was not seen with the mouse IgM used as the negative control.

(2) Immunohistostaining with Paraffin Sections

Squid cartilage was converted into small pieces followed by fixing with 10% neutral buffered formalin solution, embedding in paraffin, and prepared the paraffin sections.

The prepared sections were deparaffinized (xylene) and submitted to a hydrophilic treatment (alcohol descending series: 99.9%, 95%, 80%, 70% ethanol) followed by washing twice with 50 mmol/L tris-hydrochloric acid buffer.

Washing was performed three times with 0.01 mol/L phosphate-buffered saline and blocking was carried out for 10 minutes at room temperature using 0.3% hydrogen peroxide in methanol. Washing was performed three times with 0.01 mol/L phosphate-buffered saline and blocking was carried out for 10 minutes at room temperature using an avidin solution (Histofine, Endogenous Avidin•Biotin Blocking Kit, Nichirei Biosciences Inc.). Washing was performed three times with 0.01 mol/L phosphate-buffered saline and blocking was carried out for 10 minutes at room temperature using a biotin solution (Histofine, Endogenous Avidin•Biotin Blocking Kit, Nichirei Biosciences Inc.). Washing was performed three times with 0.01 mol/L phosphate-buffered saline and blocking was carried out for 60 minutes at room temperature using 0.1% casein solution (Wako Pure Chemical Industries, Ltd.).

The anti-CSE antibody (E-12C or E-18H), diluted to 12 μg/mL with 0.1% casein solution, was reacted for 60 minutes at 37° C. Mouse IgM (Sigma) was used here for the negative control.

Washing was performed three times with 0.01 mol/L phosphate-buffered saline followed by reaction for 10 minutes at room temperature with biotin-labeled anti-mouse IgG+IgA+IgM antibody. Washing was performed three times with 0.01 mol/L phosphate-buffered saline followed by reaction for 5 minutes at room temperature with peroxidase-labeled streptavidin. Washing was performed three times with 0.01 mol/L phosphate-buffered saline followed by immersion for 5 minutes in 50 mmol/L tris-hydrochloric acid buffer and then staining for 5 minutes with DAB (Dojindo Laboratories). After washing with ultrapure water, dehydration, clearing, and mounting were carried out by common methods.

Figure 4:
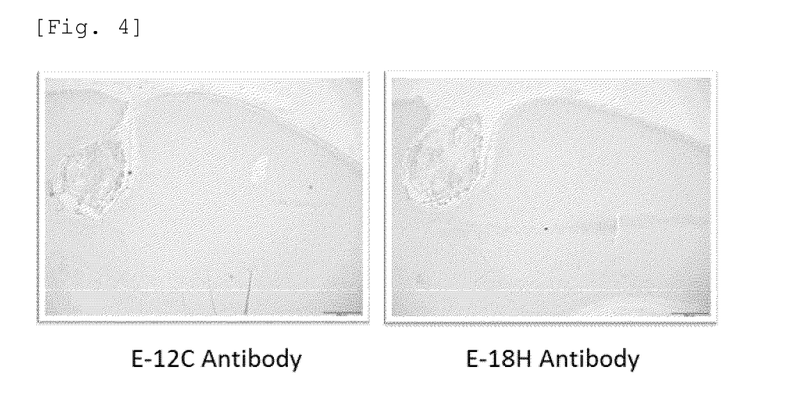
FIG. 4 is a diagram (photograph) of the staining of paraffin tissue sections using the E-12C antibody and E-18H antibody.

The obtained stained images are given in FIG. 4. Staining was seen with both the E-12C antibody and the E-18H antibody. Staining was not seen with the mouse IgM used as the negative control.

(3) Immunohistostaining of Frozen Sections Treated with C-ABC

Staining was investigated on tissue from which the chondroitin sulfates, e.g., CSE and so forth, had been removed by treatment with C-ABC.

Squid cartilage was converted into small pieces; the tissue fragments were embedded in Tissue-Tek O.C.T. Compound (Sakura Finetek Japan Co., Ltd.); freezing was performed with liquid nitrogen; and frozen sections were prepared.

The prepared sections were fixed for 10 minutes at room temperature with 10% neutral buffered formalin solution followed by washing twice with 50 mmol/L tris-hydrochloric acid buffer. After this, digestion was carried out for 120 to 180 minutes at 37° C. using C-ABC that had been diluted to 250 mU/mL using 50 mmol/L tris-hydrochloric acid buffer. The control section, which was not treated with C-ABC, was immersed for 120 to 180 minutes at 37° C. in 50 mmol/L tris-hydrochloric acid buffer. Washing was performed three times with 0.01 mol/L phosphate-buffered saline and blocking was carried out for 10 minutes at room temperature using 0.3% hydrogen peroxide in methanol. Washing was performed three times with 0.01 mol/L phosphate-buffered saline and blocking was carried out for 60 minutes at room temperature using 0.1% casein solution (Wako Pure Chemical Industries, Ltd.).

The anti-CSE antibody (E-12C), diluted to 12 μg/mL with 0.1% casein solution, was reacted for 60 minutes at 37° C. Mouse IgM (Sigma) was used here for the negative control.

Washing was performed three times with 0.01 mol/L phosphate-buffered saline followed by reaction for 10 minutes at room temperature with biotin-labeled anti-mouse IgG+IgA+IgM antibody (Histofine SAB-PO(M) Kit, Nichirei Biosciences Inc.). Washing was performed three times with 0.01 mol/L phosphate-buffered saline followed by reaction for 5 minutes at room temperature with peroxidase-labeled streptavidin (Histofine SAB-PO(M) Kit, Nichirei Biosciences Inc.). Washing was performed three times with 0.01 mol/L phosphate-buffered saline followed by immersion for 5 minutes in 50 mmol/L tris-hydrochloric acid buffer and then staining for 5 minutes with DAB (Dojindo Laboratories). After washing with ultrapure water, dehydration, clearing, and mounting were carried out by common methods.

Figure 5:
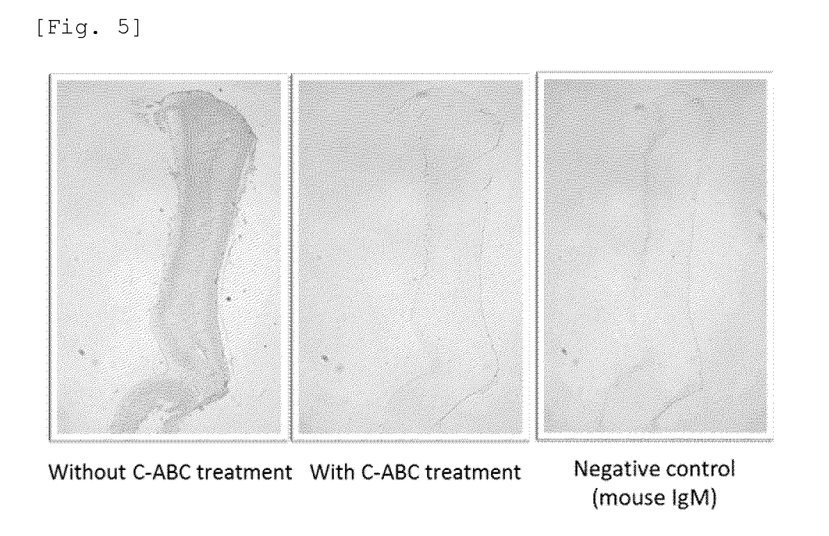
FIG. 5 is a diagram (photograph) that shows the stainability by the E-12C antibody of tissue treated with C-ABC.

The obtained stained images are given in FIG. 5. Staining was seen for the section that was not treated with C-ABC, but staining was entirely extinguished in the section that had been treated with C-ABC. The same results were also obtained with the E-18H antibody.

The disclosures in Japanese Patent Application 2014-072431 (filing date: Mar. 31, 2014) and Japanese Patent Application 2014-162968 (filing date: Aug. 8, 2014) are incorporated in their entirety in this Description by reference.

All of the literature, patent applications, and technical standards described in this Description are incorporated by reference in this Description to the same degree as if the incorporation by reference of the individual literature, patent applications, and technical standards had been specifically and individually invoked.

What is claimed is:

1. A monoclonal antibody produced by a hybridoma having International Accession number NITE BP-01808 or NITE BP-01809 wherein the antibody specifically binds chondroitin sulfate E.

2. The antibody according to claim 1 that does not specifically bind with chondroitin sulfate A, does not specifically bind with chondroitin sulfate B, and does not specifically bind with chondroitin sulfate D.

3. The antibody according to claim 2, which also does not specifically bind with any of chondroitin sulfate C, fully desulfated chondroitin sulfate C, heparin, heparan sulfate, heparosan, keratan sulfate, hyaluronic acid, and 6-O-desulfated chondroitin sulfate E.

4. The antibody according to claim 1, which is obtained by carrying out an immunization using as antigen a substance in which a lipid is linked to chondroitin sulfate E.

5. The antibody according to claim 4, wherein the lipid is dipalmitoyl-L-($\alpha$-phosphatidyl)ethanolamine.

6. A hybridoma having International Accession number selected from the group consisting of NITE BP-01808 and NITE BP-01809.

7. A method of detecting chondroitin sulfate E present in a sample, comprising performing an immunoassay comprising contacting the antibody of claim 1 with the sample to form a complex with chondroitin sulfate E present in the sample; and detecting the complex, wherein the presence of the complex indicates the presence of chondroitin sulfate E in the sample.

8. A detection kit for chondroitin sulfate E, comprising at least the antibody according to claim 1.

* * * * *

UNITED STATES PATENT AND TRADEMARK OFFICE
CERTIFICATE OF CORRECTION

PATENT NO. : 9,745,386 B2  
APPLICATION NO. : 15/128913  
DATED : August 29, 2017  
INVENTOR(S) : Ippei Watanabe Page 1 of 1

It is certified that error appears in the above-identified patent and that said Letters Patent is hereby corrected as shown below:

In the Specification

In Column 7 at Line 12 (approx.), After "etc" insert --.--.

In Column 10 at Line 34, Change "but$_4$N$^+$" to --But$_4$N$^+$--.

In Column 11 at Line 56, Change "2000λ" to --2000X--.

In Column 12 at Line 39 (approx.), Change "E-" to --6- --.

Signed and Sealed this  
Twenty-second Day of May, 2018

Andrei Iancu  
*Director of the United States Patent and Trademark Office*